United States Patent [19]

Yamakawa et al.

[11] Patent Number: 5,296,603

[45] Date of Patent: Mar. 22, 1994

[54] 3-AMINO-5-O-CHLOROBENZYL-4,5,6,7-TETRAHYDROTHIENO[3,2-C]-PYRIDINE-2-CARBOXYLIC ACID COMPOUNDS

[75] Inventors: Katsuyoshi Yamakawa; Kozo Sato, both of Minami-ashigara; Takashi Suginome, Odawara, all of Japan

[73] Assignee: Fuji Photo Film Co., Ltd., Kanagawa, Japan

[21] Appl. No.: 70,685

[22] Filed: Jun. 2, 1993

[30] Foreign Application Priority Data

Jun. 8, 1992 [JP] Japan .................................. 4-147188
Jun. 8, 1992 [JP] Japan .................................. 4-147189

[51] Int. Cl.⁵ .......................................... C07D 333/50
[52] U.S. Cl. .................................................. 546/114
[58] Field of Search ........................................ 546/114

[56] References Cited

U.S. PATENT DOCUMENTS 4,051,141 9/1977 Castaigne ............................ 546/114
4,127,580 11/1978 Braye .................................... 546/114

FOREIGN PATENT DOCUMENTS 0360293 3/1990 European Pat. Off. .
2701511 7/1977 Fed. Rep. of Germany .

OTHER PUBLICATIONS

Bulletin de la Societe Chimique de France, Part II, No. 1-2, 1978, pp. II-48 to II-54.
Chemical Abstracts, vol. 109, No. 13, Sep. 26, 1988, Columbus, Ohio, Abstract No. 110409s.
Chemical Abstracts, vol. 83, No. 23, Dec. 8, 1975, Columbus, Ohio, Abstract No. 193276q.
Chemical Abstracts, vol. 79, No. 11, Sep. 17, 1973, Columbus, Ohio, Abstract No. 66340y.
Chemical Abstracts, vol. 89, No. 19, Abstract 163,455d, p. 565, Nov. 6, 1978, Maffrand et al.
Dunn et al, *J. of Heterocyclic Chemistry*, vol. 24, No. 1, pp. 85-89, 1987.

*Primary Examiner*—C. Warren Ivy
*Assistant Examiner*—Zinna N. Davis
*Attorney, Agent, or Firm*—Sughrue, Mion, Zinn, Macpeak & Seas

[57] ABSTRACT

Intermediates of the following formulae (I) and (II):

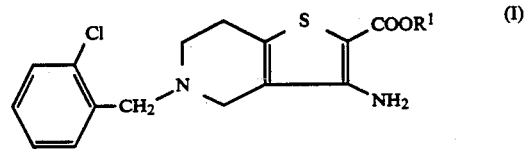

wherein $R^1$ represents a hydrogen atom or an alkyl group

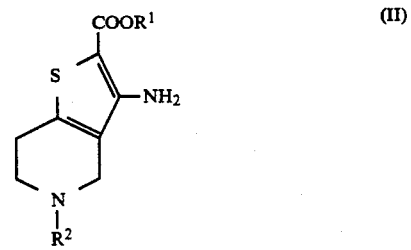

wherein $R^1$ represents a hydrogen atom or an alkyl group, and $R^2$ represents a hydrogen atom, an alkylcarbonyl group, arylcarbonyl group, alkylsulfonyl group, arylsulfonyl group, alkoxycarbonyl group or aryloxycarbonyl group and acid salt thereof are useful for synthesizing ticlopidine hydrochloride from an inexpensive and easily available compound in short steps.

9 Claims, No Drawings

3-AMINO-5-O-CHLOROBENZYL-4,5,6,7-TETRAHYDROTHIENO[3,2-C]-PYRIDINE-2-CARBOXYLIC ACID COMPOUNDS

BACKGROUND OF THE INVENTION

The present invention relates to new synthetic intermediates useful for producing ticlopidine hydrochloride having an effect of inhibiting platelet aggregation in an economical manner on an industrial scale, and a process for producing them.

Reports were made from old times on the synthesis of a 4,5,6,7-tetrahydrothieno[3,2-c]pyridine skeleton of ticlopidine hydrochloride. The processes for the synthesis can be roughly divided into two processes. One is a process wherein a thiophene derivative is used as the starting material and a tetrahydropyridine ring is closed [see, for example, Japanese Patent Publication for Opposition Purpose (hereinafter referred to as "J.P. KOKOKU") No. Sho 56-2068, Japanese Patent Unexamined Published Application (hereinafter referred to as "J.P. KOKAI") No. Sho 62-103088 and EP 439404A2] and the other is a process wherein a piperidone derivative is used as the starting material and a thiophene ring is closed (see, for example, J.P. KOKAI Nos. Sho 63-2992 and Sho 63-126883, EP 360293A2 and DE 2,701,511). The reaction schemes of them are as follows:

Known reaction scheme 1:

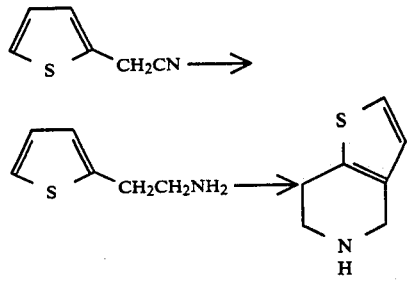

Known reaction scheme 2:

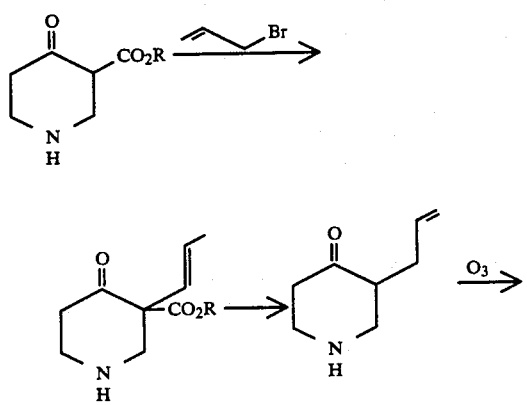

-continued
Known reaction scheme 2:

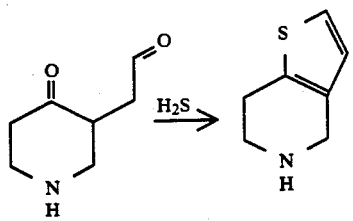

Known reaction scheme 3:

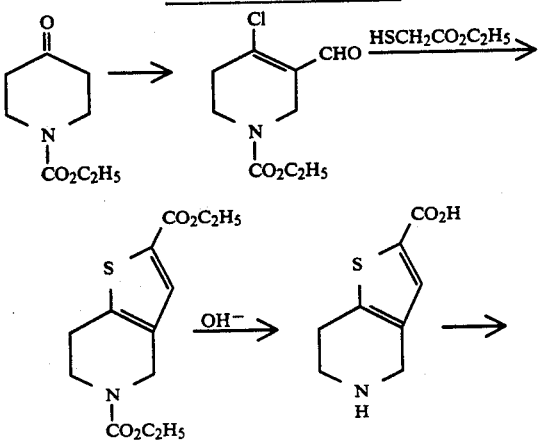

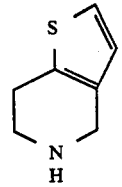

The known reaction schemes 1, 2 and 3 are disclosed in J.P. KOKAI No. Sho 62-103088, EP 360293A2 and J.P. KOKAI No. 63-2992, respectively. Although the known reaction scheme 1 comprising only a small number of the reaction steps is an advantageous process, a further improvement is demanded, since it has problems that a cyanide is used as the starting material and that side reactions occur in the course of the reduction. The investigations of the known reaction schemes 2 and 3 were started relatively recently and only a very small number of reports were proposed. Thus no process for producing the intended compound from an inexpensive starting material by short steps has been found yet.

SUMMARY OF THE INVENTION

The object of the present invention is to provide an intermediate useful for synthesizing ticlopidine hydrochloride from an inexpensive, easily available compound in short steps.

Another object of the present invention is to provide a process for producing an intermediate useful for synthesizing ticlopidine hydrochloride from an inexpensive, easily available compound in short steps.

These and other objects of the present invention will be apparent from the following description and Examples.

The first aspect of the invention relates to 3-amino-5-o-chlorobenzyl-4,5,6,7-tetrahydrothieno[3,2-c]pyridine- 2-carboxylic acid derivatives of the general formula (I):

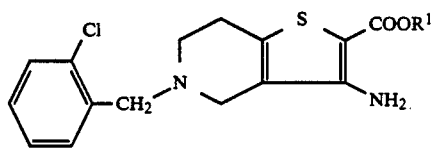

wherein $R^1$ represents a hydrogen atom or an alkyl group and acid salts thereof, and 3-amino-4,5,6,7-tetrahydrothieno[3,2-c]pyridine-2-carboxylic acid derivatives of the general formula (II):

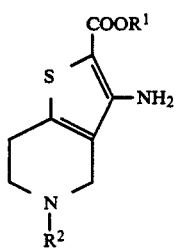

wherein wherein $R^1$ is as defined above, and $R^2$ represents a hydrogen atom, an alkylcarbonyl group, arylcarbonyl group, alkylsulfonyl group, arylsulfonyl group, alkoxycarbonyl group or aryloxycarbonyl group and acid salts of them.

The second aspect of the invention relates to a process for producing a 3-amino-4,5,6,7-tetrahydrothieno[3,2-c]pyridine-2-carboxylic acid derivative of the general formula (IIa):

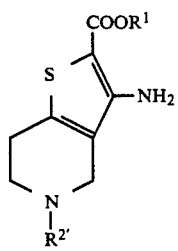

wherein $R^1$ is defined above and $R^{2'}$ represents an alkylcarbonyl group, arylcarbonyl group, alkylsulfonyl group, arylsulfonyl group, alkoxycarbonyl group or aryloxycarbonyl group which comprises reacting a 3-cyano-4-piperidone derivative of the general formula (III):

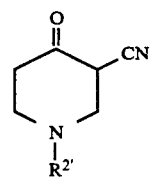

wherein $R^{2'}$ is as defined above with a sulfonic acid halide of the general formula (IV):

 (IV)

wherein $R^3$ represents an alkyl group or aryl group and X represents a halogen to form a 3-cyanotetrahydropyridine derivative of the general formula (V):

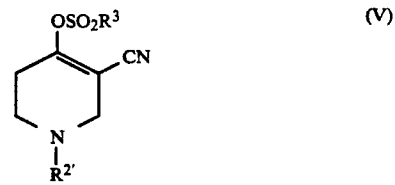

wherein $R^{2'}$ and $R^3$ are as defined above and reacting this product with a thioglycolic acid of the general formula (VI):

 (VI)

wherein $R^1$ is as defined above
or its ester in the presence of a base.

The third aspect of the invention relates to a process for producing a 3-amino-5-o-chlorobenzyl-4,5,6,7-tetrahydrothieno[3,2c]pyridine-2-carboxylic acid derivative of the general formula (I), which comprises decomposing the amide bond of a compound of the general formula (IIa) under an acidic condition to obtain a 3-amino-4,5,6,7tetrahydrothieno[3,2-c]pyridine-2-carboxylic acid derivative of the general formula (IIb):

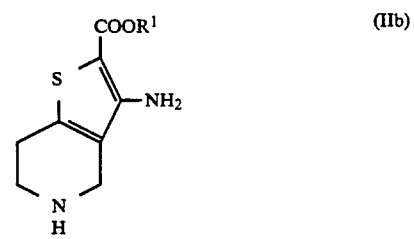

wherein $R^1$ is as defined above and then o-chlorobezylating this product.

DETAILED EXPLANATION OF PREFERRED EMBODIMENTS

The compounds of the general formulae (I) and (II) are synthetic intermediates useful for producing ticlopidine hydrochloride by the following reaction scheme:

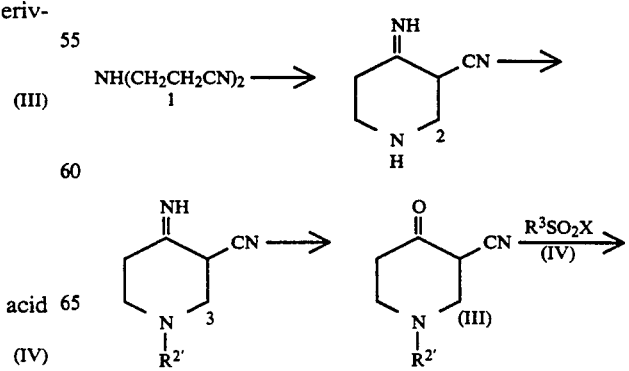

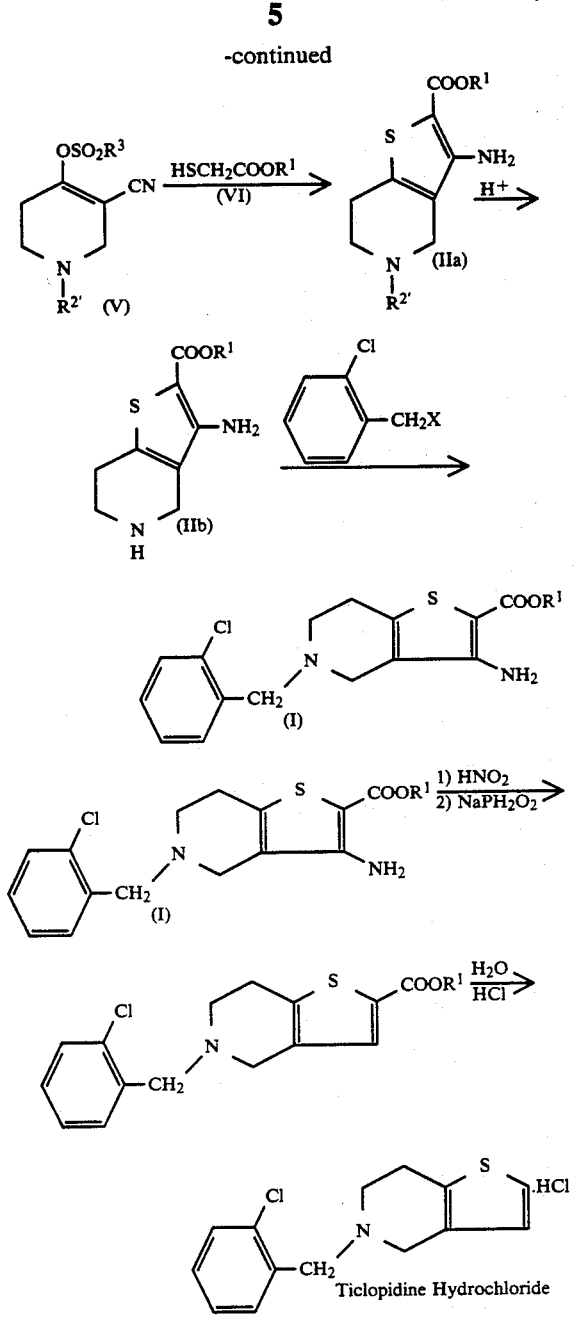

R[1] in the above general formulae (I) and (II) represents a hydrogen atom or alkyl group. Examples Of the alkyl group include straight chain or branched alkyl groups having 1 to 20 carbon atoms, preferably 1 to 8 carbon atoms (such as methyl, ethyl, propyl, butyl and 2-ethylhexyl groups).

R[2] in the general formula (II) represents a hydrogen atom, an alkylcarbonyl group, arylcarbonyl group, alkylsulfonyl group, arylsulfonyl group, alkoxycarbonyl group or aryloxycarbonyl group. Examples of the groups include alkylcarbonyl groups having preferably 1 to 20 carbon atoms, more preferably 1 to 8 carbon atoms (such as formyl and acetyl groups), arylcarbonyl groups having preferably 6 to 20 carbon atoms, more preferably 6 to 14 carbon atoms (such as benzoyl and o-chlorobenzoyl groups) the alkylcarbonyl group include, alkylsulfonyl groups having preferably 1 to 20 carbon atoms, more preferably 1 to 8 carbon atoms (such as methanesulfonyl and butanesulfonyl groups), arylsulfonyl groups having preferably 6 to 20 carbon atoms, more preferably 6 to 14 carbon atoms (such as benzenesulfonyl and ptoluenesulfonyl groups), alkoxycarbonyl groups having preferably 2 to 20 carbon atoms, more preferably 2 to 9 carbon atoms (such as methoxycarbonyl, ethoxycarbonyl, t-butoxycarbonyl and benzyloxycarbonyl groups) and aryloxycarbonyl groups having preferably 7 to 20 carbon atoms, more preferably 7 to 15 carbon atoms (such as phenoxycarbonyl and p-nitrophenoxy groups). In these groups represented by R[2], particularly preferred are alkylcarbonyl groups and arylcarbonyl groups having 1 to 8 carbon atoms.

The acids capable of forming the acid salts with the compounds of the general formulae (I) and (II) include inorganic acids such as hydrochloric acid, sulfuric acid, etc.; and organic acids such as acetic acid, p-toluenesulfonic acid, etc. The most preferred salt is hydrochloride.

Examples of the compounds of the general formulae (I) and (II) of the present invention are listed in Tables 1 to 4.

Namely, a compound of the general formula (III) is synthetized from 3,3,'-iminodipropionitrile 1 which is the starting material and easily available on the market at a low cost. Subsequently, a compound of the general formula (IIa) is synthetized through the compound of the general formula (V). The amide bond of the compound of the general formula (IIa) is decomposed under an acidic condition to easily obtain a compound of the general formula (IIb), which is then treated with an o-chlorobenzyl halide to obtain a compound of the general formula (I) in a high yield. Ticlopidine hydrochloride is produced by deaminating the thus-obtained compound of the general formula (I) according to an ordinary method (diazotization and reduction), and hydrolyzing and decarboxylating the deaminated compound under an acidic condition.

The detailed description will be made on these compounds according to the present invention hereafter.

TABLE 1

| No. | R[1] |
|---|---|
| 1 | H— |
| 2 | CH$_3$— |
| 3 | C$_2$H$_5$— |
| 4 | C$_4$H$_9$— |
| 5 | C$_4$H$_9$CH(C$_2$H$_5$)CH$_2$— |

TABLE 2

| No. | R[2] | R[1] |
|---|---|---|
| 6 | H— | H— |
| 7 | H— | CH$_3$— |
| 8 | H— | C$_2$H$_5$— |
| 9 | H— | C$_4$H$_9$— |
| 10 | H— | C$_4$H$_9$CH(C$_2$H$_5$)CH$_2$— |

TABLE 2-continued

Examples of the compounds of formula (II)

$$\text{(II)}$$

structure: piperidine fused thiophene with $R^2-N$, $S$, $COOR^1$, $NH_2$

| No. | $R^2$ | $R^1$ |
|---|---|---|
| 11 | CHO— | $CH_3-$ |
| 12 | CHO— | $C_2H_5-$ |
| 13 | CHO— | $C_4H_9-$ |
| 14 | CHO— | $C_4H_9CH(C_2H_5)CH_2-$ |
| 15 | CHO— | H— |
| 16 | $CH_3CO-$ | $CH_3-$ |
| 17 | $CH_3CO-$ | $C_2H_5-$ |
| 18 | $CH_3CO-$ | $C_4H_9-$ |
| 19 | $CH_3CO-$ | $C_4H_9CH(C_2H_5)CH_2-$ |
| 20 | $CH_3CO-$ | H— |
| 21 | $CH_3CO-$ | $CH_3O_2CH_2CH_2-$ |
| 22 | $CH_3CO-$ | $HOCH_2CH_2-$ |

TABLE 3

Examples of the compounds of formula (II)

| No. | $R^2$ | $R^1$ |
|---|---|---|
| 23 | φCO— | $CH_3-$ |
| 24 | φCO— | $C_2H_3-$ |
| 25 | φCO— | $C_4H_9-$ |
| 26 | φCO— | $C_4H_9CH(C_2H_5)CH_2-$ |
| 27 | φCO— | H— |
| 28 | o-Cl-C₆H₄-CO— | $CH_3-$ |
| 29 | o-Cl-C₆H₄-CO— | $C_4H_9CH(C_2H_5)CH_2-$ |
| 30 | o-Cl-C₆H₄-CO— | H— |
| 31 | $CH_3SO_2-$ | $CH_3-$ |
| 32 | $CH_3SO_2-$ | $C_4H_9-$ |
| 33 | $CH_3SO_2-$ | $C_4H_9CH(C_2H_5)CH_2-$ |
| 34 | $CH_3SO_2-$ | H— |

TABLE 4

Examples of the compounds of formula (II)

| No. | $R^2$ | $R^1$ |
|---|---|---|
| 35 | 2,4,6-trimethylphenyl-$SO_2-$ | $CH_3-$ |
| 36 | 2,4,6-trimethylphenyl-$SO_2-$ | H— |
| 37 | p-$CH_3$-C₆H₄-$SO_2-$ | $CH_3-$ |
| 38 | p-$CH_3$-C₆H₄-$SO_2-$ | H— |
| 39 | $CH_3OCO-$ | $CH_3-$ |
| 40 | $CH_3OCO-$ | H— |
| 41 | t-$C_4H_9OCO-$ | $CH_3-$ |
| 42 | t-$C_4H_9OCO-$ | $C_4H_9-$ |
| 43 | t-$C_4H_9OCO-$ | $C_4H_9CH(C_2H_5)CH_2-$ |
| 44 | t-$C_4H_9OCO-$ | H— |

The detailed description will be made on the process according to the present invention hereafter.

The 3-cyano-4-piperidone derivative of the general formula (III) can be easily synthetized from easily available 3,3'-im inodipropionitrile 1 by the above-mentioned reaction scheme.

In detail, 3,3'-imidodipropionitrile 1 is treated with a strong base (such as metallic sodium, sodium hydride or sodium alkoxide) to obtain a ring-closed compound 2 J. Am. Chem. Soc., 69, 1535 (1947)], which is then reacted with an acid halide or acid anhydride which leaves $R^{2'}$ as the residue to form a compound 3. The compound 3 is hydrolyzed with hydrochloric acid to obtain a 3-cyano-4-piperidone derivative of the general formula (III). It is also possible to synthesize this compound in one pot without isolating the compounds 2 and 3.

Examples of $R^{2'}$ in compound 3 and the general formula (III ) include alkylcarbonyl groups having preferably 1 to 20 carbon atoms, more preferably 1 to 8 carbon atoms (such as formyl and acetyl groups), arylcarbonyl groups having preferably 6 to 20 carbon atoms, more preferably 6 to 14 carbon atoms (such as benzoyl and o-chlorobenzoyl groups), alkylsulfonyl groups having preferably 1 to 20 carbon atoms, more preferably 1 to 8 carbon atoms (such as methanesulfonyl and butanesulfonyl groups), arylsulfonyl groups having preferably 6 to 20 carbon atoms, more preferably 6 to 14 carbon atoms (such as benzenesulfonyl and p-toluenesulfonyl groups), alkoxycarbonyl groups having preferably 2 to 20 carbon atoms, more preferably 2 to 9 carbon atoms (such as methoxycarbonyl, ethoxycarbonyl, t-butoxycarbonyl and benzyloxycarbonyl groups) and aryloxycarbonyl groups having preferably 7 to 20 carbon atoms, more preferably 7 to 15 carbon atoms (such as phenoxycarbonyl and p-nitrophenoxy groups). In these groups represented by $R^{2'}$, particularly preferred are alkylcarbonyl groups and arylcarbonyl groups having 1 to 8 carbon atoms.

The production of the compound of the general formula (V) from the compound of the general formula (III) is conducted by reacting the latter with a sulfonic acid halide of the general formula (IV).

Examples of $R^3$ in the general formula (IV) include alkyl groups having preferably 1 to 20 carbon atoms, more preferably 1 to 8 carbon atoms (such as methyl and butyl groups), and aryl groups having Preferably 6 to 20 carbon atoms, more preferably 6 to 14 carbon atoms (such as phenyl and p-tolyl groups). In these groups represented by $R^3$, particularly preferred is methyl, phenyl or p-tolyl group. X is chlorine, bromine or iodine. Particularly desirable X is chlorine or bromine. The molar ratio of the sulfonic acid halide to the compound of the general formula (III) is 0.5/1 to 2/1, preferably 0.9/1 to 1.2/1.

The solvents usable for this reaction include, for example, acetonitrile, dimethylacetamide, dimethylformamide, dime thylimidazolidinone, tetrahydrofuran, diethyl ether, dioxane, benzene, toluene, xylene, ethanol, methanol, dichloromethane, chloroform and ethyl acetate. Particularly preferred is dimethylformamide, dimethylacetamide or acetonitrile.

This reaction is conducted preferably in the presence of a base such as sodium methoxide, sodium carbonate, potassium carbonate, potassium t-butoxide, triethylamine, diazabicyclo[5,4,0]undecene (DBU), 2,6-lutidine, collidine or pyridine. Pyridine used as the base can act also as the solvent. The amount of the base used is usually 1 to 100 mol, preferably 1 to 10 mol and more preferably 1 to 1.5 mol, per mol of the 3-cyanopiperidone derivative.

The reaction temperature is usually 0° to 25° C., preferably 0° to 15° C. The reaction time which markedly varies depending on the molar ratio of the starting materials to be reacted and reaction temperature is usually 1 to 4 hours, preferably 1 to 2 hours.

After completion of the reaction, the reaction solution is poured into cold dilute hydrochloric acid, and the product is extracted with a suitable solvent and concentrated to isolate the compound of the general formula (V) in the form of, for example, a colorless liquid. However, in the practical production, this product can be subjected to the subsequent reaction without isolation.

The detailed description will be made on the process for the production of compound of the general formula (IIa) from the compound of the general formula (V) and thioglycolic acid of the general formula (VI) or an estr thereof.

When the compound of the general formula (V) is isolated, it must be dissolved in a solvent. The solvent usable in this step can be the same as that used for the above-described reaction.

The amount of the thioglycolic acid derivative of the general formula (VI) is 0.5 to 2 mol, preferably 0.9 to 1.2 mol, per mol of the compound of the general formula (V).

The bases which can be present in the reaction system include, for example, sodium hydride, sodium methoxide, sodium carbonate, potassium carbonate, potassium t-butoxide, triethylamine and diazabicyclo[5,4,0]undecene (DBU). particularly preferred bases are triethylamine, DBU, etc. These bases can be used either singly or in combination of two or more of them. The amount of the base is usually 1 to 10 mol, preferably 1 to 3 mol, per mol Of the compound of the general formula (VI).

When the compound of the general formula (V) is not isolated, the above-described thioglycolic acid derivative and base are added in amounts in the above-described ranges to the solution.

When the compound of the general formula (VI) is thioglycolic acid ($R^1=H$), replacement reaction of —SH group of thioglycolic acid with $-OSO_2R^3$ group of the compound of the general formula (V) is previously conducted by the treatment with the base in the same manner as that described above and then the resultant product is reacted with an alkylating agent in the presence of a base or, alternatively, thioglycolic acid is reacted with an alcohol in the presence of an acid catalyst to esterify the carboxyl group of thioglycolic acid and the resultant ester is treated with a strong base to conduct the ringclosing reaction, thereby forming a compound of the general formula (IIa). Examples of the alkylating agents include methyl iodide, dimethyl sulfate, diazomethane, ethyl orthoformate and ethyl orthoacetate. Examples of the alcohols include methanol, ethanol and 2-ethylhexanol. The acid catalysts used in the esterification with the alcohol include sulfuric acid, hydrochloric acid, aromatic sulfonic acids such as p-toluenesulfonic acid and Lewis acids such as boron fluoride etherate.

The reaction temperature is usually 0° to 25° C., preferably 0° to 15° . The reaction time which markedly varies depending on the molar ratio of the starting materials and reaction temperature is usually 1 to 4 hours, preferably 1 to 2 hours.

After completion of the reaction, the intended product can be isolated by an ordinary method such as neutralization, extrusion, extraction, washing, concentration or crystallization. The product can be purified, if necessary, by recrystallization, column chromatography or the like.

Next, the compound of the general formula (IIb) is produced by decomposing the amide bond of the compound of the general formula (IIa) under an acidic condition. The acid used in this step is hydrochloric acid, sulfuric acid, hydrobromic acid or the like. The solvent usable in this step is water, an alcohol such as methanol or ethanol, cellosolves, acetic acid or the like. They can be used either singly or in the form of a mixture of them. Particularly preferred solvent is an alcohol such as methanol or ethanol. The amount of the acid is usually 2 to 10 mol per mol of the compound of the general formula (IIa). The reaction temperature is usually 20° to 100° C., preferably 20° to 80° C. The reaction time which markedly varies depending on the varieties of the solvent and acid used, relative amounts of them and reaction temperature is usually 1 to 4 hours, preferably 1 to 2 hours. After completion of the reaction, the intended product can be isolated by an ordinary method such as neutralization, extrusion, extraction, washing, concentration or crystallization. The product can be purified, if necessary, by recrystallization, column chromatography or the like.

The compound of the general formula (I) can be obtained by o-chlorobenzylating the compound of the general formula (IIb).

The o-chlorobenzylating agents used for the o-chlorobenzylation include o-chlorobenzyl halides such as o-chlorobenzyl chloride, o-chlorobenzyl bromide and o-chlorobenzyl iodide. The amount of the o-chlorobenzylating agent used is 1 to 1.5 mol, preferably 1 to 1.2 mol, per mol of the compound of the general formula (IIb). This reaction must be conducted in the presence of a base. Examples of the bases include inorganic bases such as sodium carbonate and potassium carbonate; and organic bases such as tertiary amines, e.g. triethylamine and diazabicyclo[5,4,0]undecene, and tetrabutylammonium hydroxide. The solvents usable for this reaction include, for example, dimethylformamide, dimethylacetamide and acetonitrile. The reaction temperature is usually 20° to 100° C., preferably 20° to 80° C. The reaction time which markedly varies depending on the varieties of the solvent and base, the molar ratio and reaction temperature is usually 1 to 8 hours, preferably 1 to 4 hours. After completion of the reaction, the intended product can be isolated by an ordinary method such as neutralization, extrusion, extraction, washing, concentration or crystallization. The product can be purified, if necessary, by recrystallization, column chromatography or the like.

EXAMPLES

Example 1

Compound No. 16

8.3 g (0.05 mol) of 1-acetyl-3-cyanopiperidine-4-one was dissolved in 11.9 g (0.15 mol) of pyridine. 5.7 g (0.05 mol) of methanesulfonyl chloride was added dropwise to the resultant solution under cooling with ice and then the resultant mixture was stirred at room temperature for 30 min. Then a solution of 5.4 g (0.05 mol) of methyl thioglycolate and 19.3 g (0.1 mol $CH_3ONa$) of 28% solution of sodium methylate in methanol was stirred for 5 min and then added to the reaction solution obtained as described above. The resultant mixture was stirred at room temperature for 30 min. The reaction solution was cooled with ice. 9.6 g (0.05 mol $CH_3ONa$) of 28% solution of sodium methylate in methanol was added to the reaction solution and the resultant mixture was stirred at room temperature for 30 min.

After completion of the reaction, 800 ml of water was added to the reaction solution. After neutralization (pH 5 to 6) with hydrochloric acid followed by extraction with ethyl acetate (600 ml×2), the ethyl acetate layer was washed with 500 ml of 3 N aqueous sodium hydroxide solution and then with 500 ml of water. Ethyl acetate was distilled off under reduced pressure and the residue was recrystallized from acetonitrile to obtain 5.8 g (46%) of methyl 1-acetyl-3-amino-4,5,6,7-tetrahydrothieno[3,2-c]pyridine-2-carboxylate.

Melting point: 196.5°~198.5° C.

From the following results of the determination of NMR spectrum, it was supposed that the compound was a mixture of two amide bond rotational isomers (A and B) (A:B=1:1.6).

$^1$H-NMR (200 MHz) δppm (DMSO- $d_6$, room temp.):
A 2.08(s, 3H), 2.65(t, 2H, J=5.7Hz), 3.70(t, 2H, J=5.7Hz),
3.70(s, 2H), 4.33(s, 2H), 6.53(s, 2H);
B 2.10(s, 3H), 2 78(t, 2H, J=5.0Hz), 3.70(t, 2H, J=5.0Hz),
3.70(s, 3H), 4.33(s, 2H), 6.53(s, 2H).

Example 2

Compound No. 18

16.6 g (0.1 mol) of 1-acetyl-3-cyanopiperidine-4-one was dissolved in 23.8 g (0.3 mol) of pyridine. 11.5 g (0.1 mol) of methanesulfonyl chloride was added dropwise to the resultant solution under cooling with ice and then the resultant mixture was stirred at room temperature for 30 min. Then 14.8 g (0.1 mol) of n-butyl thioglycolate was added to the resultant mixture. Then the reaction solution was cooled with ice. 40.4 g (0.2 mol) of triethylamine was added dropwise to the reaction solution.

The reaction solution was stirred at room temperature for 30 min and then 38.6 g (0.2 mol $CH_3ONa$) of 28% solution of sodium methylate in methanol was added to the solution under cooling with ice, and the resultant mixture was stirred at room temperature for 30 min.

After completion of the reaction, 600 ml of water was added to the reaction solution to form crystals, which was neutralized (pH~7) with hydrochloric acid. The crystals were taken by filtration, washed with water and recrystallized from acetonitrile to obtain 20.4 g (69%) of n-butyl 1-acetyl-3-amino-tetrahydrothieno[3,2-c]pyridine-2carboxylate.

Melting point: 133.5° to 135° C.

From the following results of determination of NMR spectrum, it was supposed that the compound was a mixture of two amide bond rotational isomers (A and B) (A:B=1:1.5).

$^1$H-NMR (200 MHz) δppm (DMSO-$d_6$, room temp.),
A 0.91(t, 3H, J=7.7Hz), 1.36(tq, 2H, J=7.7, 7.0 Hz), 1.62(tt, 2H,
J=7.0, 6.7Hz), 2.07(s, 3H), 2.65(t, 2H, J=5.3 Hz), 3.72(t,
2H, J=5.3Hz), 4.13(t, 2H, J=6.7 Hz), 4.33(s, 2H), 6.53(s, 2H);
B 0.91(t, 3H, J=7.7. Hz), 1.36(tq, 2H, J=7.7, 7.0 Hz), 1.62(tt, 2H,
J=7.0, 6.7 Hz), 2.10(s, 3H), 2.79(t, 2H, J=5.0 Hz), 3.68(t,
2H, J=5.0 Hz), 4.13(t, 2H, J=6.7 Hz), 4.33(s, 2H), 6.53(s, 2H).

Example 3

Compound No. 23

Compound No. 23 was synthetized in substantially the same manner as that of Example 2 except that 1-benzoyl-3-cyanopiperidine-4-one and metyl thioglycolate were used instead of 1-acetyl-3-cyanopiperidine-4one and n-butyl thioglycolate, respectively.

Melting point: 173.5° to 176° C.

From the following results of determination of NMR spectrum, it was supposed that the compound was a mixture of two amide bond rotational isomers (A and B) (A:B=1:3.5).

$^1$H-NMR (200 MHz) δppm ( DMSO-$d_6$, room temp.):
A 2.78(bs, 2H), 3.70(s, 3H), 3.88(bs, 2H), 4.31(bs, 2H), 6 45(bs, 2H), 7.47(m, 5H);
B 2.78(bs, 2H), 3.60(bs, 2H), 3.70(s, 3H), 4.50(bs, 2H), 6.62(bs, 2H), 7.47(m, 5H).

Example 4

Compound No. 25

Compound No. 25 was synthetized in substantially the same manner as that of Example 2 except that 1-benzoyl-3-cyanopiperidine-4-one and ethyl thioglycolate were used instead of 1-acetyl-3-cyanopiperidine-4one and n-butyl thioglycolate, respectively.

Melting point: 128.5° to 130° C.

From the following results of determination of NMR spectrum, it was supposed that the compound was a mixture of two amide bond rotational isomers (A and B) (A:B=1:2.7).

$^1$H-NMR (200 MHz) δppm (DMSO-$d_6$, room temp.):
A 0.91(t, 3H, J=7.0 Hz), 1.36(tq, 2H, J=7.0, 6.5 Hz), 1.62(tt, 2H, J=6.5, 6.2 Hz), 2.78(bs, 2H), 3.88(bs, 2H), 4.15(t, J=6.2 Hz),
4.33(bs, 2H), 6.42(bs, 2H), 7.47(m, 5H);
B 0.91(t, 3H, J=7.0 Hz), 1.36(tq, 2H, J=7.0, 6.5 Hz), 1.62(tt, 2H,
J=6 5, 6.2 Hz), 2.78(bs, 2H), 3.58(bs, 2H), 4.15(t, J=6.2 Hz),
4.50(bs, 2H), 6.57(bs, 2H), 7.47(m, 5H).

Example 5

Compound No. 28

Compound No. 28 was synthetized in substantially the same manner as that of Example 2 except that 1-o-chlorobenzoyl-3-cyanopiperidine-4-one and methyl thioglycolate were used instead of 1-acetyl-3-cyanopiperidine-4-one and n-butyl thioglycolate, respectively.

Melting point: 178° to 179.5° C.

From the following results of determination of NMR spectrum, it was supposed that the compound was a mixture of two amide bond rotational isomers (A and B) (A:B=1:2).

$^1$H-NMR (200 MHz) δppm (DMSO-d$_6$, room temp.):
A 2.82(t, 2H, J=5.0 Hz), 3.68(s, 3H), 3.96(m, 2H), 4.08(s, 2H)
6.42(bs, 2H), 7.45(m, 4H);
B 2.72(t, 2H, J=5.0 Hz), 3.45(t, 2H, J=5.0 Hz), 3.71(s, 3H),
4.46(d, 1H, J=16.7 Hz), 4.68(d, 1H, J=16.7 Hz), 6.62(bs, 2H),
7.45(m, 4H)

Example 6

Compound No. 37

Compound No. 37 was synthetized in substantially the same manner as that of Example 2 except that 1-p-toluenesulfonyl-3-cyanopiperidine4-one and methyl thioglycolate were used instead of 1-acetyl-3-cyanopiperidine-4-one and n-butyl thioglycolate, respectively.

Melting point: 171.5° to 173.5° C.

$^1$H-NMR (200 MHz) δppm (DMSO-d$_6$, room temp.):
2.40(s, 3H), 2.76(t, 2H, J=6.0 Hz), 3.31(t, 2H, J=6.0 Hz), 3.69(s, 3H),
3.93(s, 2H), 6.53(s, 2H), 7.45(d, 2H, J=8.7 Hz), 7.71(d, 2H, J=8.7 Hz)

Example 7

Compound No. 39

Compound No. 39 was synthetized in substantially the same manner as that of Example 2 except that 1-methoxycarbonyl-3-cyanopiperidine-4-one and methyl thioglycolate were used instead of 1-acetyl-3-cyanopiperidine-4-one and n-butyl thioglycolate, respectively.

Melting point: 166.5° to 168° C.

$^1$H-NMR (200 MHz) δppm ( DMSO-d$_6$, room temp.):
2.70(t, 2H, J=5.6 Hz), 3.65(t, 2H, J=5.6 Hz), 3.65(s, 3H), 3.70(s, 3H),
4.28(s, 2H), 6.55(s, 2H).

Example 8

Compound No. 6

An aqueous solution obtained by dissolving 9.1 g of sodium hydroxide in 90 ml of water was added to 5.8 g (46%) of methyl 5-acetyl-3-amino-4,5,6,7-tetrahydrothieno[3,2-c]pyridine-2carboxylate (Compound No. 16) obtained in Example 1 and the resultant mixture was heated under reflux for 2 hours. After cooling followed by neutralization with concentrated hydro-chloric acid, the solvent was distilled off. Methanol was added to the residue and the crystals thus formed were taken by filtration and thoroughly washed with water to obtain 1.7 g of 3-amino-4,5,6,7-tetrahydrothieno[3,2-c]pyridine-2-carboxylic acid. Yield: 38%.

Melting point: 146-147° C. (dec.)

$^1$H—NMR (200 M Hz)
δppm (DMSO-d$_6$+D$_2$O): 2.60(2H, t, J=6.0 Hz), 2.95(2H, t, J=6.0
Hz), 3.52(2H, s).

Example 9

Hydrochloride salt of Compound No. 7

20 ml of methanol and then 5.1 ml of concentrated hydrochloric acid were added to 2.54 g of methyl 5-acetyl-3-amino-4,5,6,7tetrahydrothieno[3,2-c]pyridine-2-carboxylate (Compound No. 16) obtained in Example 1. The resultant mixture was heated under reflux for 4 hours. After cooling, the crystals thus formed were taken by filtration to obtain 1.70 g (68%) of methyl 3-amino-4,5,6,7-tetrahydrothieno[3,2-c]pyridine-2-carboxylate hydrochloride.

Melting point: 270° C. or above $^1$H—NMR (200 M Hz)
δppm (DMSO-d$_6$): 2.95(2H, t, J=6.0 Hz), 3.40(2H, t, J=6.0 Hz), 3.71(3 H, s), 3.95(2H, t), 6.60(2H, s), 9.76(2H, s).

Example 10

Hydrochloride salt of Compound No. 9

40 ml of n-butanol and then 5.1 ml of concentrated hydrochloric acid were added to 2.96 g of n-butyl 5-acetyl-3-amino-4,5,6,7-tetrahydrothieno[3,2-c]pyridine-2-carboxylate (Compound No. 18) obtained in Example 2. The resultant mixture was heated in a steam bath for 2 hours. The solvent was distilled off. 20° ml of acetonitrile was added to the reaction mixture and the crystals thus formed were taken by filtration to obtain 1.86 g (64%) of n-butyl 3-amino-4,5,6,7-tetrahydrothieno[3,2-c]pyridine-2-carboxylate hydrochloride.

Melting point: 269°-271° C. (dec.)

$^1$H—NMR (200 M Hz)
δppm ( DMSO-d$_6$): 0.91(t, 3H, J=7.3 Hz), 1.37(tq, 2H, J=7.3, 7.0
Hz), 1.60(tt, 2H, J=7.0. 6.7 Hz), 2.95(t, 2H, J=5.7 Hz), 3.35(t, 2H,
J=5.7 Hz), 3.95(s, 2H), 4.15(t, 2H, J=6.7 Hz), 6.58(s, 2H), 9.72(s, 2H).

Example 11

Compound No. 2

2.48 g of methyl 3-amino-4,5,6,7-tetrahydrothieno[3,2-c]pyridine-2-carboxylate hydrochloride (Compound No. 7) obtained in Example 9 and 1.61 g of o-chlorobenzyl chloride were dispersed in 20 ml of acetonitrile. 3.1 ml of triethylamine was added to the dispersion and the resultant mixture was heated under reflux for 4 hours. After cooling, ethyl acetate and water were added thereto. After fractionation followed by washing with water, the product was dried over Glauber's salt. The solvent was distilled off and the residue was purified by column chromatography (n-hexane / ethyl acetate=1/1). The crystals were formed with a solvent mixture of n-hexane / ethyl acetate to obtain 1.42 g (42%) of methyl 3-amino-5-o-chlorobenzyl-4,5,6,7-tetrahydrothieno[3,2-c]pyridine-2- carboxylate.

Melting point: 120°–121° C.

$^1$H—NMR (200 M Hz)

δppm (DMSO-$d_6$): 2.75(bs, 2H), 3.35(s, 2H), 3.69(s, 3H), 3.77(s, 2H), 6.38(s, 2H), 7.32(m, 4H).

What is claimed is:

1. A compound of the formula (I):

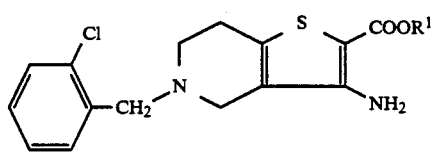

wherein $R^1$ represents a hydrogen atom or an alkyl group or an acid salt thereof.

2. The compound or an acid salt thereof according to claim 1 wherein $R^1$ is an alkyl group.

3. The compound or an acid salt thereof according to claim 2 wherein $R^1$ is an alkyl group having 1 to 20 carbon atoms.

4. A compound of the formula (II):

wherein $R^1$ represents a hydrogen atom or an alkyl group, and $R^2$ represents a hydrogen atom, an alkylcarbonyl group, arylcarbonyl group, alkylsulfonyl group, arylsulfonyl group, alkoxycarbonyl group or aryloxycarbonyl group or an acid salt thereof.

5. The compound or an acid salt thereof according to claim 4 wherein $R^1$ is an alkyl group and $R^2$ is an alkylcarbonyl group, arylcarbonyl group, alkylsulfonyl group, arylsulfonyl group, alkoxycarbonyl group or aryloxycarbonyl group.

6. The compound or an acid salt thereof according to claim 5 wherein $R^2$ is an alkylcarbonyl group, arylcarbonyl group, alkoxycarbonyl group or aryloxycarbonyl group.

7. The compound or an acid salt thereof according to claim 6 wherein $R^1$ is an alkyl group having 1 to 20 carbon atoms and $R^2$ is an alkylcarbonyl group having 1 to 20 carbon atoms, arylcarbonyl group having 6 to 20 carbon atoms, alkoxycarbonyl group having 2 to 20 carbon atoms or aryloxycarbonyl group having 7 to 15 carbon atoms.

8. The compound or an acid salt thereof according to claim 4 wherein $R^1$ is a hydrogen atom or alkyl group and $R^2$ is a hydrogen atom.

9. The compound or an acid salt thereof according to claim 8 wherein $R^1$ is an alkyl group having 1 to 20 carbon atoms.

* * * * *